United States Patent
Shigemori et al.

(10) Patent No.: US 7,704,204 B2
(45) Date of Patent: Apr. 27, 2010

(54) INTRABODY INTRODUCED DEVICE AND MEDICAL DEVICE

(75) Inventors: Toshiaki Shigemori, Hachioji (JP); Takeshi Mori, Machida (JP)

(73) Assignee: Olympus Corporation, Tokyo (JP)

( * ) Notice: Subject to any disclaimer, the term of this patent is extended or adjusted under 35 U.S.C. 154(b) by 992 days.

(21) Appl. No.: 11/137,022

(22) Filed: May 24, 2005

(65) Prior Publication Data
US 2006/0004253 A1 Jan. 5, 2006

(30) Foreign Application Priority Data
May 24, 2004 (JP) .............................. 2004-153894

(51) Int. Cl.
*A61B 1/04* (2006.01)
(52) U.S. Cl. .......................... 600/109; 600/160; 348/65
(58) Field of Classification Search ................. 600/109, 600/160; 348/65, 68, 74
See application file for complete search history.

(56) References Cited

U.S. PATENT DOCUMENTS

| | | | | |
|---|---|---|---|---|
| 3,686,434 A | * | 8/1972 | Lemelson | 360/18 |
| 4,015,076 A | * | 3/1977 | Ishiodori | 348/623 |
| 4,398,215 A | * | 8/1983 | Osaka | 380/221 |
| 5,115,319 A | * | 5/1992 | Arai et al. | 348/230.1 |
| 5,138,451 A | * | 8/1992 | Shinkawa et al. | 348/524 |
| 5,179,446 A | * | 1/1993 | Hong | 348/333.07 |
| 5,333,055 A | * | 7/1994 | Murata et al. | 348/239 |
| 5,604,531 A | | 2/1997 | Iddan et al. | |
| 6,366,311 B1 | * | 4/2002 | Monroe | 348/148 |
| 6,437,824 B1 | * | 8/2002 | Suzuki et al. | 348/222.1 |
| 6,933,977 B2 | * | 8/2005 | Egashira | 348/333.12 |
| 2003/0213495 A1 | * | 11/2003 | Fujita et al. | 128/899 |
| 2004/0042621 A1 | * | 3/2004 | Hausman | 381/2 |

FOREIGN PATENT DOCUMENTS

JP 2002-345743 12/2002

* cited by examiner

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

In transmitting images picked up by an intrabody introduced device to outside a test body, synchronizing signals of the image signal are set to signal patterns in the same high-frequency band as for the image signal and not used for the image signal. This enables a receiver to stably binarize the synchronizing signal and thus to acquire favorable image signal. For example, in a clipping circuit provided in a signal processing circuit in a capsule type endoscope (an example of an intrabody introduced device), image information of a high-intensity portion is clipped out of image information acquired by an imaging section and a pattern generation circuit allocates signal patterns within the clipped intensity range as horizontal and vertical synchronizing signals.

9 Claims, 9 Drawing Sheets

INTRABODY INTRODUCED DEVICE AND MEDICAL DEVICE

CROSS-REFERENCE TO RELATED APPLICATION

This application is based upon and claims the benefit of priority from prior Japanese Patent Application No. 2004-153894, filed May 24, 2004, the entire contents of which is incorporated herein by reference.

BACKGROUND OF THE INVENTION

1. Field of the Invention

The present invention relates to an intrabody introduced device, which is introduced into a test body, or a medical device including the intrabody introduced device. This type of intrabody introduced device includes, for example, a swallowable capsule type endoscope.

2. Description of the Related Art

In recent years, a capsule type endoscope having an imaging function and a wireless function has emerged as one of the intrabody introduced devices in the endoscope area. The capsule type endoscope is swallowed by a test subject as a test body for observation (examination) and then moves inside the stomach, the small intestine, or other organs (in the body cavity) by the organs' peristaltic motion for the observation period until it is excreted naturally from the test subject. The capsule type endoscope sequentially takes images of the inside of the test body by using the imaging function while it moves inside the body cavity.

Image information captured in the body cavity by the capsule type endoscope during the observation of the organs while moving inside thereof is transmitted to an external device provided outside the test body by using a wireless function (radio communication or the like) of the capsule type endoscope and then stored in a memory provided inside the external device. The test subject carries the external device, whereby the test subject is not restrained in behavior during the observation period until the capsule type endoscope is excreted after the test subject swallows the capsule type endoscope. After the observation, images of the inside of the body cavity are displayed on a screen of a display or the like on the basis of the image information stored in the memory of the external device, whereby a doctor or a nurse can make a diagnosis.

In this type of capsule type endoscope, there is a swallowable capsule type endoscope such as, for example, one disclosed in Japanese Laid-Open Patent Publication (Kokai) No. 2002-345743. This capsule type endoscope includes a battery for power supply and an LED for emitting an illumination light by means of the power supplied from the battery. The capsule type endoscope then takes images of the inside of the test body illuminated by the illumination light by using an imaging device to acquire the image information and wirelessly transmits the image information from a transmitter circuit. In the aforementioned capsule type endoscope, the image information is composed of a frame and it is wirelessly transmitted with a horizontal synchronizing signal and a vertical synchronizing signal added at the beginning of the image frame. With synchronization based on the synchronizing signals, a receiver distinguishes the beginning of the image line for scanning the image information when capturing the images.

The capsule type endoscopes of the prior art can incorrectly recognize synchronizing signals as image information, and in such case, may use the synchronizing signals having signal patterns included in the image information. Accordingly, signals in a low-frequency band lower than the frequency of the image information are used as synchronizing signals in some cases. If the frequency band of the synchronizing signals is set to the foregoing frequency band (in the low-frequency band), however, a phenomenon of a fluctuation in the DC level of the signals appears.

Therefore, when the synchronizing signals are binarized at a predetermined level (a threshold value), a margin of the threshold is decreased due to the fluctuation of the DC level, so the receiver has a difficulty to binarize the synchronizing signals.

This invention has an object to provide an intrabody introduced device in which its synchronizing signals are well binarized in the receiver and good quality of images can be obtained.

BRIEF SUMMARY OF THE INVENTION

According to one aspect of the present invention, there is provided an intrabody introduced device introduced into a test body to acquire information on an inside of the test body. The intrabody introduced device has a lighting section for emitting an illumination light for illuminating the inside of the test body and an imaging section for acquiring image information on the inside of the test body illuminated by the lighting section. In addition, the intrabody introduced device has an allocating section for allocating a part of signal levels of image information to synchronizing signals when wirelessly outputting the picked-up image information.

For example, in the same high-frequency band as the image signals, signals having signal levels not used for image signals are assumed synchronizing signals. Thereby, the fluctuation in the DC levels of the synchronizing signals can be reduced to stabilize binarization of the synchronizing signals. Furthermore, the image signals can be favorably separated from the synchronizing signals.

The allocating section can include, for example, a clipping section for clipping signal levels of at least a part of the image information acquired by the imaging section and a setting section for setting the signal levels clipped by the clipping section to the synchronizing signals.

In this condition, a receiver can distinguish the image signals clipped by the clipping section from the synchronizing signals set by the setting section by means of the signal levels. The clipping section clips the signal levels of the image signals so as to prevent the signal levels of the image signals from being mixed with the signal levels allocated to the synchronizing signals.

The allocating section can include, for example, a converting section for converting signal levels of specific image information to signal levels clipped by the clipping section and a setting section for setting the signal levels of the specific image information converted by the converting section to the synchronizing signals.

It is preferable to clip signal levels in the vicinity of the maximum and/or minimum value without clipping middle signal levels where a lot of valid information exists.

The method of converting the signal levels of the image information so that they are included in a given range to prevent an inclusion of the signal levels used for the synchronizing signals is not limited to clipping. For example, it may be a method of multiplying a signal level of an image by a given coefficient (smaller than 1).

According to another aspect, the present invention can be a medical device comprising the intrabody introduced device and a receiver for receiving radio signals transmitted from the intrabody introduced device outside the test body.

The intrabody introduced device or the medical device according to the present invention is capable of setting synchronizing signals in the same high-frequency band as image signals and in signal patterns not used for image signals. This enables the receiver to stably binarize the synchronizing signals and thus acquire favorable image signals.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

Preferred embodiments of the invention will be described below with reference to the accompanying drawings.

The present invention is not limited to these embodiments, but various changes may be made without departing from the scope of the invention.

Figure 1:
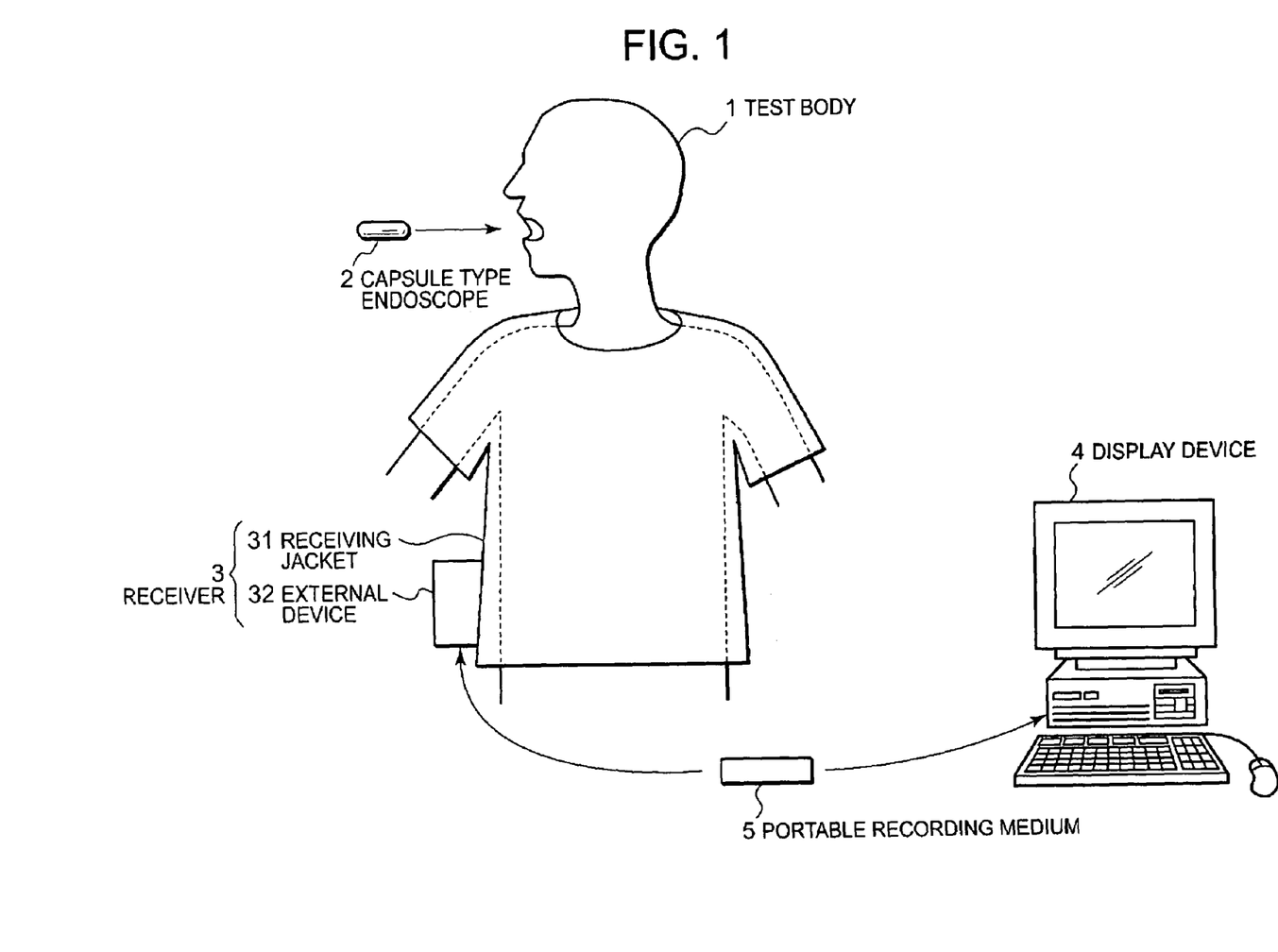
FIG. 1 is a schematic diagram showing a general configuration of a wireless intrabody information acquisition system including an intrabody introduced device according to a first embodiment.

Referring to FIG. 1, there is shown a schematic diagram of a general configuration of a wireless intrabody information acquisition system including an intrabody introduced device according to a first embodiment. This wireless intrabody information acquisition system will now be described below by giving an example of a capsule type endoscope as the intrabody introduced device. Those skilled in the art will appreciate that the capsule type endoscope is used by way of example only and that other intrabody introduced devices can also be used without departing from the spirit and scope of the claimed invention. In FIG. 1, the wireless intrabody information acquisition system comprises a receiver 3 having a wireless receiving function and a capsule type endoscope (intrabody introduced device) 2, which is introduced into a test body 1 to capture images of the inside of the body cavity and transmit data such as image signals to the receiver 3. The wireless intrabody information acquisition system further comprises a display device 4 for displaying the images of the inside of the body cavity on the basis of the image signals received by the receiver 3 and a portable recording medium 5 for passing data between the receiver 3 and the display device 4. The receiver 3 includes a receiving jacket 31 worn by the test body 1 and an external device 32 for processing radio signals received. The capsule type endoscope 2 and the receiver 3 are included in a medical device according to the present invention.

The display device 4 is for use in displaying the images of the inside of the body cavity captured by the capsule type endoscope 2 and displays the images on the basis of data acquired by the portable recording medium 5. The display device 4 has a configuration like a work station, for example. Specifically, the display device 4 may be configured to display images directly by means of a CRT display or a liquid crystal display. Furthermore, the display device 4 may be configured to output images to another medium other than a display, such as a printer.

The portable recording medium 5 is removable from the external device 32 and the display device 4. When the portable recording medium 5 is inserted into such devices, it can output or record information. In the first embodiment, the portable recording medium 5 is inserted into the external device 32 and records data transmitted from the capsule type endoscope 2 while the capsule type endoscope 2 moves inside the body cavity of the test body 1. After the capsule type endoscope 2 is excreted from the test body 1, in other words, after completion of imaging of the inside of the test body 1, the portable recording medium 5 is then removed from the external device 32 and inserted into the display device 4 and the display device 4 reads out the data recorded by the portable recording medium 5. The data is passed between the external device 32 and the display device 4 by means of the portable recording medium 5 in this manner, thereby permitting the test body 1 to move more freely during imaging of the inside of the body cavity than in a case where the external device 32 is directly connected to the display device 4 via a fixed line. For example, the aforementioned portable recording medium 5 can be a CompactFlash® (CF) memory. Note that, however, the portable recording medium 5 has been used for passing data between the external device 32 and the display device 4 here, but it is not necessarily limited to this. For example, another internal recording device (a hard disk or the like) may be used instead of the external device 32 and be connected to the display device 4 via a fixed line or wirelessly for passing data to the display device 4.

Figure 2:
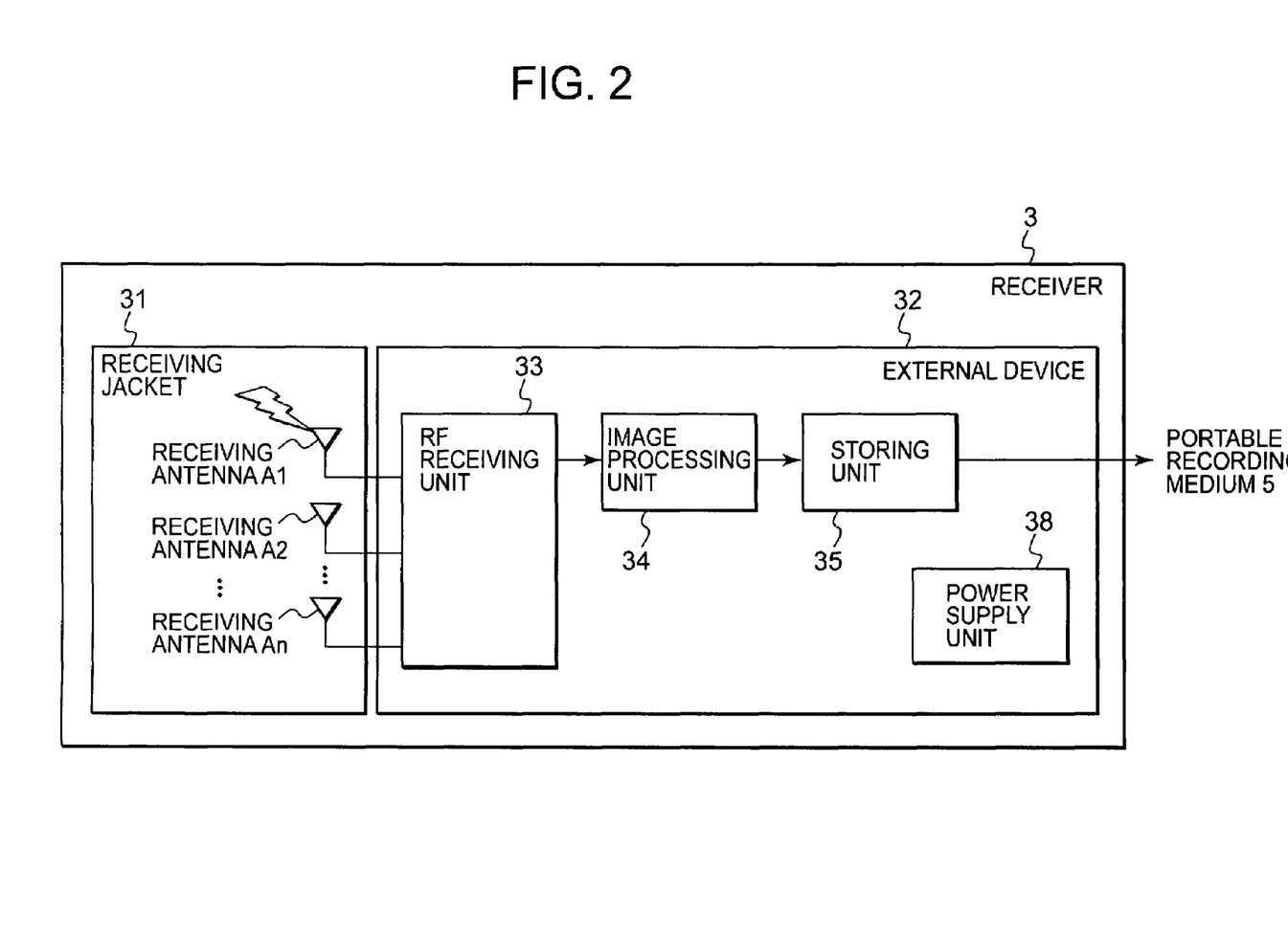
FIG. 2 is a block diagram showing an internal configuration of a receiver according to the first embodiment shown in FIG. 1.

Subsequently, the configuration of the receiver will be described with reference to the block diagram shown in FIG. 2. The receiver 3 has a function of receiving image information on the inside of the body cavity wirelessly transmitted from the capsule type endoscope 2. As shown in FIG. 2, the receiver 3 is provided with the receiving jacket 31 and the external device 32. The receiving jacket 31 has a form enabling the test body 1 to wear it, having receiving antennas A1 to An. The external device 32 processes radio signals received via the receiving jacket 31. The receiving antennas A1 to An can be directly adhered to an outer surface of the test body, instead of being provided in the receiving jacket 31. The receiving antennas A1 to An can also be detachable from the receiving jacket 31.

The external device 32 includes an RF receiving unit 33, an image processing unit 34, a storing unit 35, and a power supply unit 38. The RF receiving unit 33 performs given signal processing such as demodulation for radio signals received by the receiving antennas A1 to An and extracts image information acquired by the capsule type endoscope 2 out of the radio signals. The image processing unit 34 performs image processing necessary for the image information extracted by the RF receiving unit 33. The storing unit 35 records the image information image-processed by the image processing unit 34. In this manner, the external device 32 performs signal processing of the radio signals transmitted from the capsule type endoscope 2. In the first embodiment, the image information is recorded into the portable recording medium 5 via the storing unit 35. Furthermore, the power supply unit 38 has a given capacitor or AC adapter. The components of the external device 32 use power as driving energy supplied from the power supply unit 38.

Subsequently, the configuration of the capsule type endoscope 2 will be described by using the block diagram shown in FIG. 3. The capsule type endoscope 2 includes a light emitting device (LED) 20, an LED driving circuit 21, a charge coupled device (CCD) 23, a CCD driving circuit 24, a signal processing circuit 25, an image pickup timing generation circuit 26, and a pattern generation circuit 40 (See FIG. 4). The light emitting device (LED) 20 is a lighting section for irradiating an examined area in the body cavity of the test body 1. The LED driving circuit 21 controls a driven state of the LED 20. The charge coupled device (CCD) 23 is an imaging section that captures images of the inside of the body cavity formed by a reflected light from the area irradiated by the LED 20. The CCD driving circuit 24 controls a driven state of the CCD 23. The signal processing circuit 25 processes image signals output from the CCD 23 to acquire image information in a desired format. The image pickup timing generation circuit 26 is a clock generating section for outputting reference clock pulses for use in giving driving timing such as the timing of turning on the LED 20 or the image pickup timing of the CCD 23. The pattern generation circuit 40 generates synchronizing signals described later. The capsule type endoscope 2 further includes an RF transmission unit 27 for modulating the picked-up image information to RF signals and a transmission antenna 28 as a radio transmission section for wirelessly transmitting the RF signals output from the RF transmission unit 27. The capsule type endoscope 2 further includes a system control circuit 29 for controlling operations of the LED driving circuit 21, the CCD driving circuit 24, and the RF transmission unit 27 and a battery 30 for supplying power to these electrical apparatuses. The CCD 23, the CCD driving circuit 24, the signal processing circuit 25, and the image pickup timing generation circuit 26 are included in the imaging section 22. With the provision of these mechanisms, the capsule type endoscope 2 acquires the image signals of the examined area, irradiated by the LED 20, by the CCD 23 while it is introduced into the test body 1, using the reference clock pulses that represent a desired image pickup timing. The acquired analog image signals are submitted to signal processing by the signal processing circuit 25 on the basis of the reference clock pulses, converted to RF signals by the RF transmission unit 27, and then transmitted to the outside of the test body 1 via the transmission antenna 28.

Figure 3:
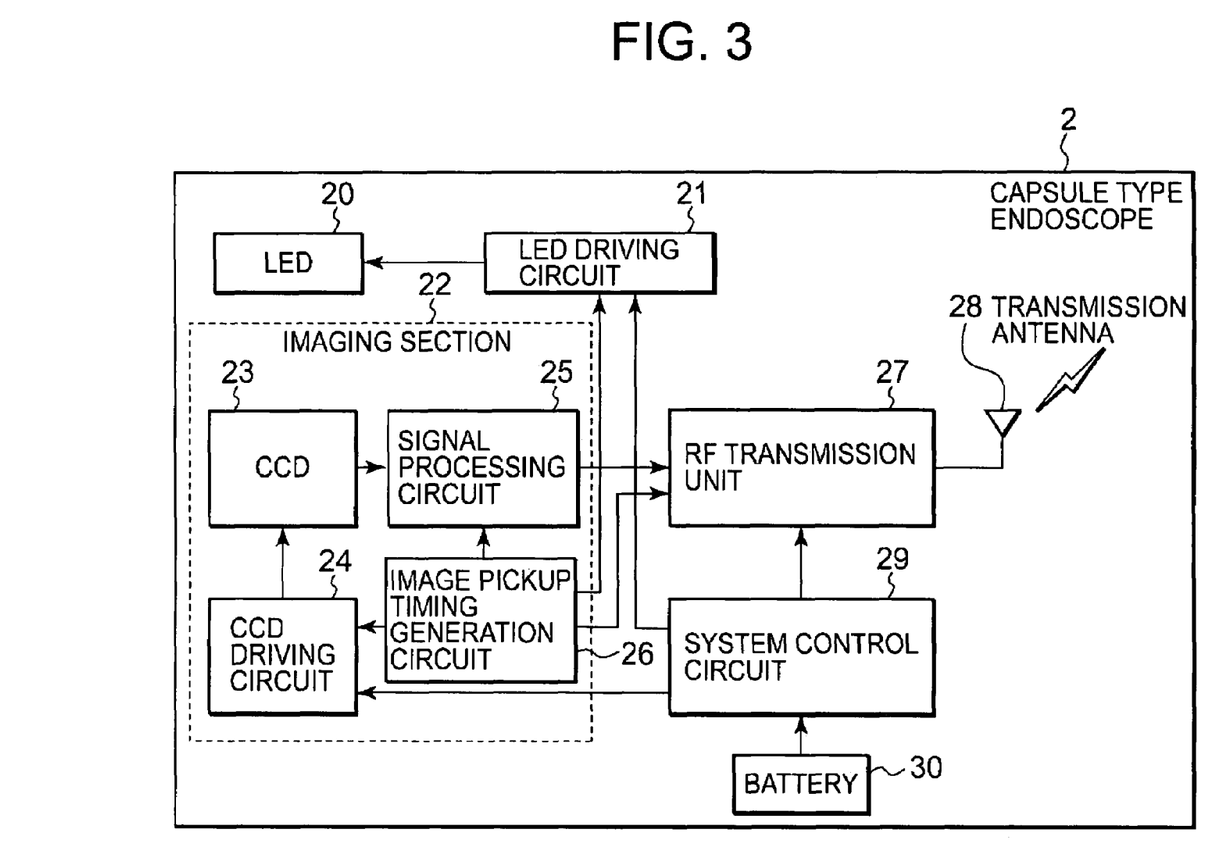
FIG. 3 is a block diagram showing an internal configuration of a capsule type endoscope according to the first embodiment shown in FIG. 1.
Figure 4:
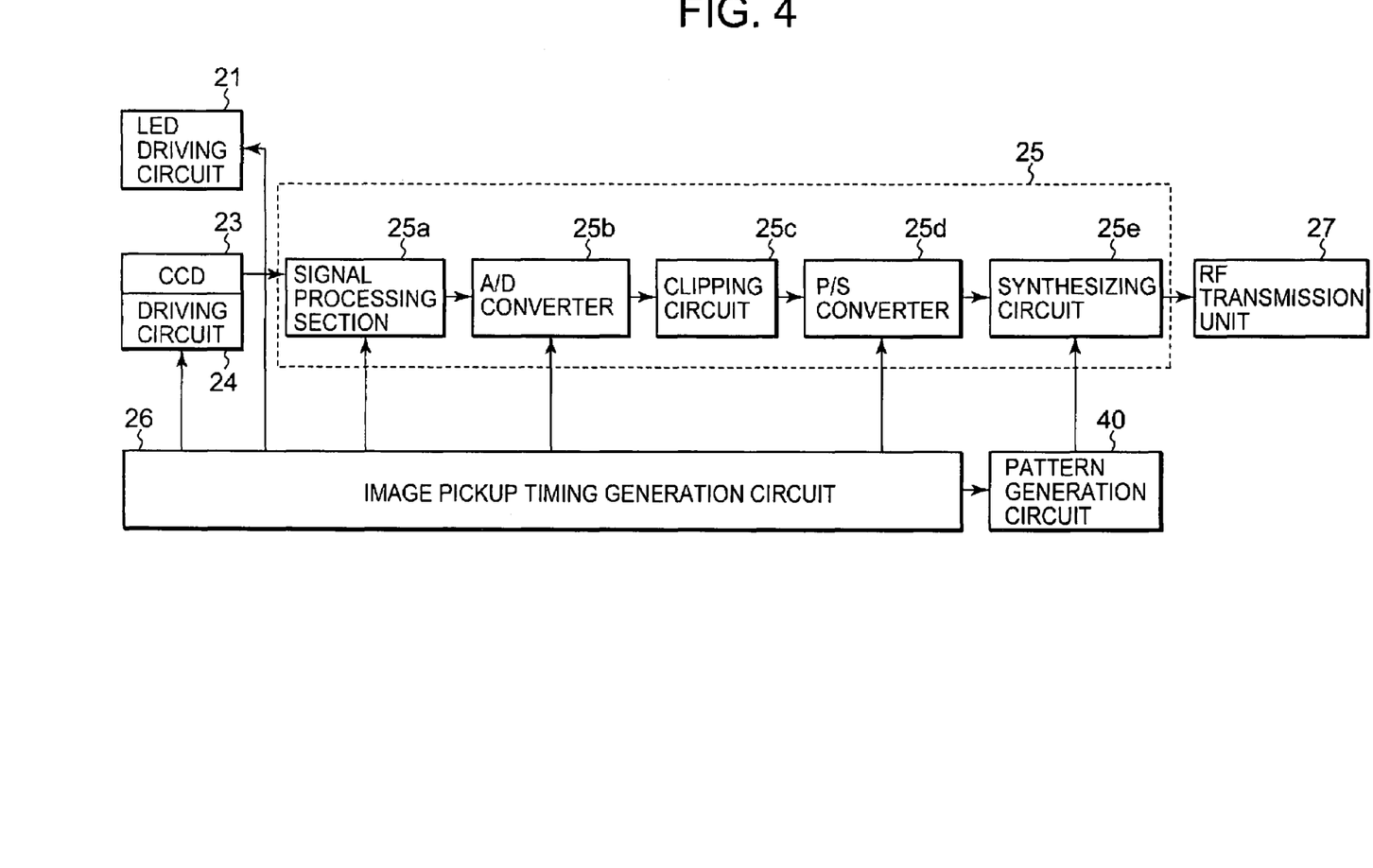
FIG. 4 is a block diagram showing the first embodiment of a configuration of an image pickup timing system shown in FIG. 3.

Referring to FIG. 4, there is shown a block diagram of a configuration of the image pickup timing system shown in FIG. 3. In FIG. 4, the image pickup timing generation circuit 26 outputs the reference clock pulses as the base of driving timing to the LED driving circuit 21, the CCD driving circuit 24, the signal processing circuit 25, and the pattern generation circuit 40 that generates synchronizing signals. The signal processing circuit 25 includes a signal processing section 25a, an A/D converter 25b, a clipping circuit 25c, a P/S converter 25d, and a synthesizing circuit 25e. The signal processing section 25a performs desired signal processing for the image signals output from the CCD 23. The A/D converter 25b converts the analog image signals to digital image information. The clipping circuit 25c clips given signal levels of image information. The P/S converter 25d performs a parallel-to-serial conversion of image information. The synthesizing circuit 25e synthesizes the image information with synchronizing signals. The clipping circuit 25c and the pattern generation circuit 40 constitute a first allocating section according to the present embodiment. The clipping circuit 25c has a function of a clipping section and the pattern generation circuit has a function of a setting section.

Figure 5:
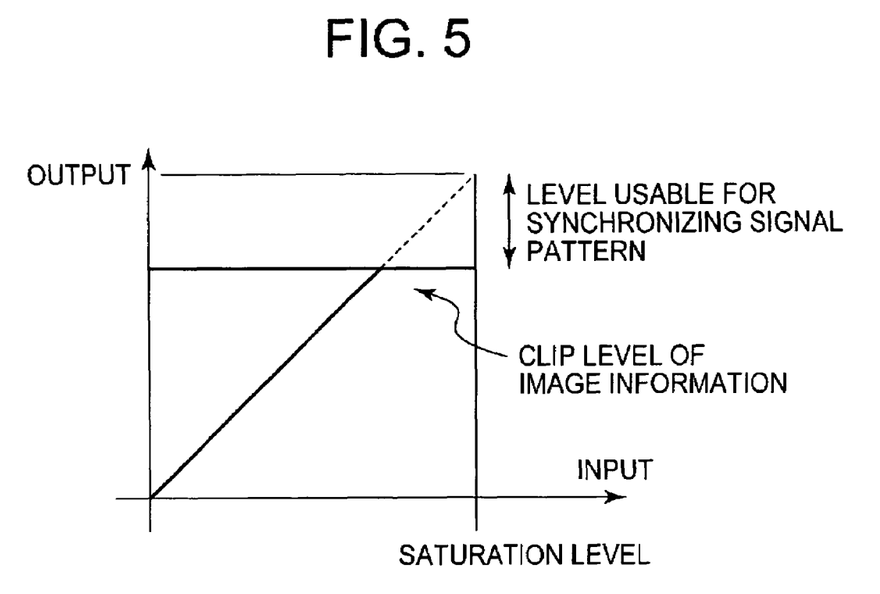
FIG. 5 is a diagram showing a signal level of image information for explaining an example of a clipping operation of image information in the clipping circuit shown in FIG. 4.

As shown in FIG. 5, the clipping circuit 25c clips a high-intensity portion of intensities of the image information. If the image information is represented by 8-bit signal levels (signal patterns) of 0 to 255, for example, the clipping circuit 25c clips image information of the high-intensity portion having signal patterns of 240 to 255. Specifically, if there is an input of image information of the high-intensity portion (for example, signal patterns of 240 to 255) from the A/D converter 25b, the clipping circuit 25c converts it to image information of a signal pattern of 239 and outputs it to the P/S converter 25d. An encoding circuit for encoding signals can be used as the clipping circuit 25c.

The pattern generation circuit 40 allocates the signal patterns in the intensity range clipped by the aforementioned clipping circuit 25c as a horizontal synchronizing signal and a vertical synchronizing signal. The pattern generation circuit 40 generates a horizontal synchronizing signal having a signal pattern of 240 and a vertical synchronizing signal having a signal pattern of 250 and then outputs them to the synthesizing circuit 25e. The signal patterns of these synchronizing signals generated by the pattern generation circuit 40 are in the high-frequency band of which frequency the image information also uses. In this manner, the synchronizing signals are set in the same frequency band as the image information, thereby a fluctuation in DC levels of the signals that may occur when the synchronizing signals are set in a low-frequency band can be prevented. Therefore, a wide margin for a threshold can be secured in binarization, thereby facilitating the detection of the synchronizing signals in the receiver. The synthesizing circuit 25e adds the horizontal and vertical synchronizing signals generated by the pattern generation circuit 40 to the clipped and parallel-to-serial converted image information and outputs it to the RF transmission unit 27. The RF transmission unit 27 forms the image information into a frame and wirelessly transmits it to the outside of the test body with the horizontal synchronizing signal and the vertical synchronizing signal added at the beginning of the image frame.

Figure 6:
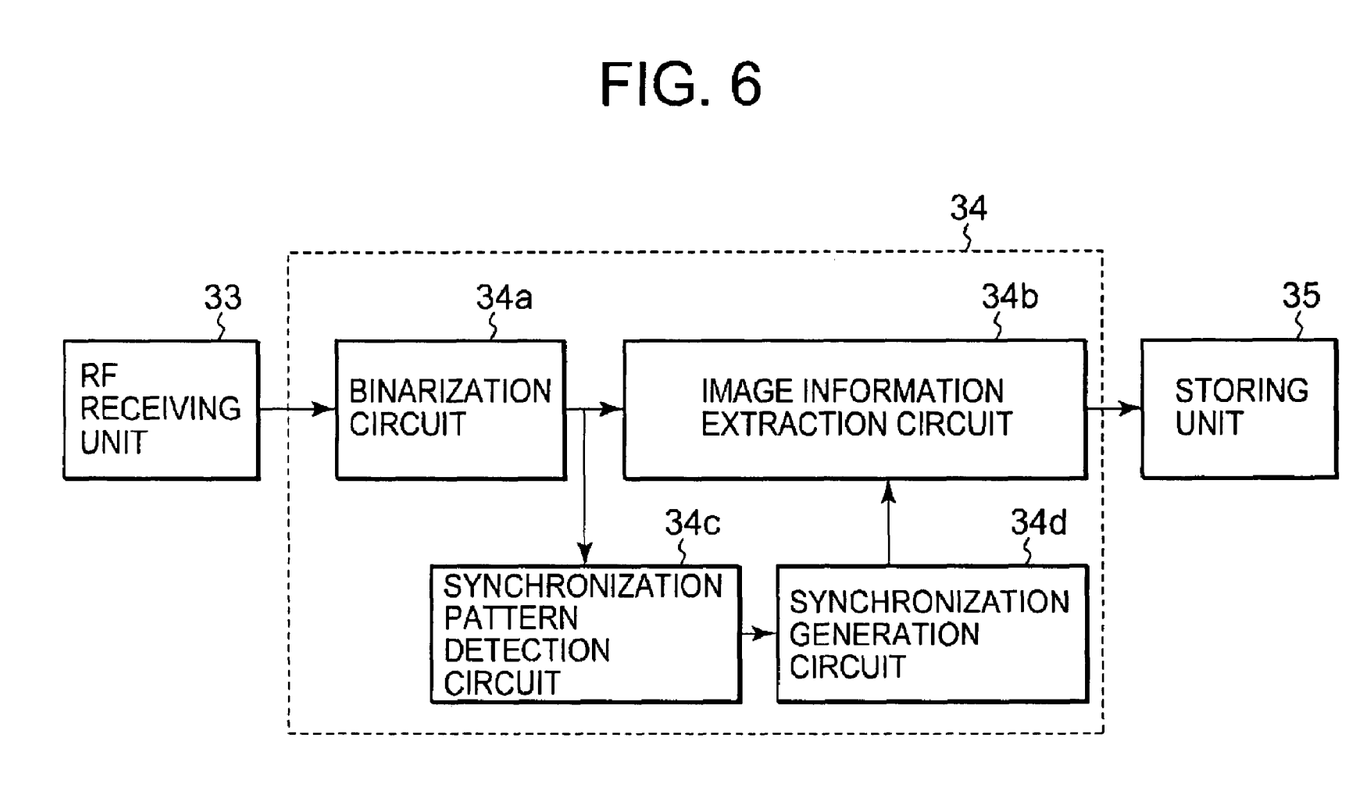
FIG. 6 is a block diagram showing a first embodiment of a detailed configuration of an image processing unit in the external device shown in FIG. 2.

Referring to FIG. 6, there is shown a block diagram of an example of a detailed configuration of the image processing unit 34 in the external device 32 shown in FIG. 2. In FIG. 6, the image processing unit 34 includes a binarization circuit 34a, an image information extraction circuit 34b, a synchronization pattern detection circuit 34c, and a synchronization generation circuit 34d. The binarization circuit 34a binarizes information input from the RF receiving unit 33. The image information extraction circuit 34b extracts image information from the binarized information. The synchronization pattern detection circuit 34c is an extracting section for detecting a signal pattern of a synchronizing signal from the binarized information. The synchronization generation circuit 34d generates a horizontal synchronizing signal and a vertical synchronizing signal from the signal patterns detected by the synchronization pattern detection circuit 34c. In the image processing unit 34, the image information extraction circuit 34b extracts image information for each frame on the basis of the horizontal and vertical synchronizing signals input from the synchronization generation circuit 34d and stores it into the storing unit 35.

Figure 7:
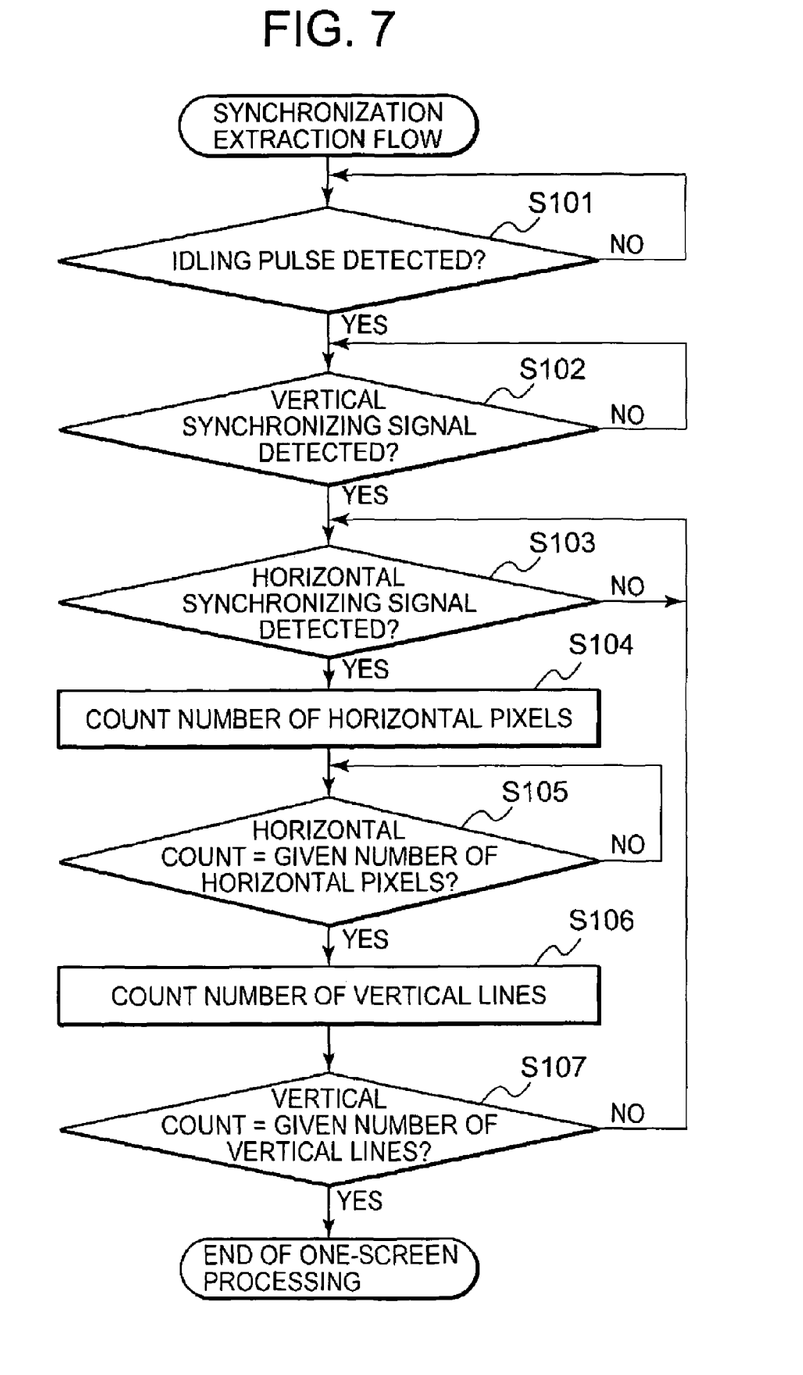
FIG. 7 is a flowchart for explaining a processing operation of the image processing unit shown in FIG. 6.

The image processing unit 34 performs processing shown in the flowchart of FIG. 7. Specifically, the synchronization pattern detection circuit 34c detects whether an idling pulse is added at the beginning of the vertical synchronizing signal (step 101). If it detects the idling pulse (step 101-YES), it subsequently detects signal patterns of the vertical synchronizing signal and the horizontal synchronizing signal having high frequencies in the same frequency band as for the image signals (steps 102 and 103).

If the synchronization pattern detection circuit 34c detects the signal patterns of the vertical and horizontal synchronizing signals in the above, the synchronization generation circuit 34d outputs these synchronizing signals to the image information extraction circuit 34d. The image information extraction circuit 34b counts the number of horizontal pixels on the basis of the horizontal synchronizing signal (step 104). It then determines whether the pixel count has reached the total number of horizontal pixels (step 105).

Counting the number of horizontal pixels is continued until the pixel count reaches the total number of horizontal pixels. When the pixel count reaches the total number of horizontal pixels (step 105-YES), the image information extraction circuit 34b subsequently counts the number of vertical lines on the basis of the vertical synchronizing signal (step 106). It then determines whether the vertical line count has reached the total number of vertical lines (step 107).

Also counting the number of vertical lines is continued until the count reaches the total number of vertical lines. When the vertical line count reaches the total number of vertical lines, the image information extraction circuit 34b determines that the image processing for one screen has completed and performs image processing for the next screen.

As stated above, image information of the high-intensity portion is clipped out of the acquired image information and signal patterns in the clipped intensity range are allocated as horizontal and vertical synchronizing signals and wirelessly transmitted to the receiver in the first embodiment. Therefore, the synchronizing signals can be set to signal patterns in the same high-frequency band as for image signals but not used for the image signals, thereby preventing a fluctuation in DC level of the signals and permitting a wide margin for a threshold for binarization. This enables the receiver to binarize synchronizing signals stably and to obtain favorable image signals.

In the first embodiment, the image information of the high-intensity portion is clipped and the signal patterns are allocated to the horizontal and vertical synchronization signals. In this condition, however, it is possible that it may be difficult to distinguish between the synchronizing signals because the two types of synchronizing signals have similar signal patterns and the difference in the signal level between the synchronizing signals is small.

Figure 8:
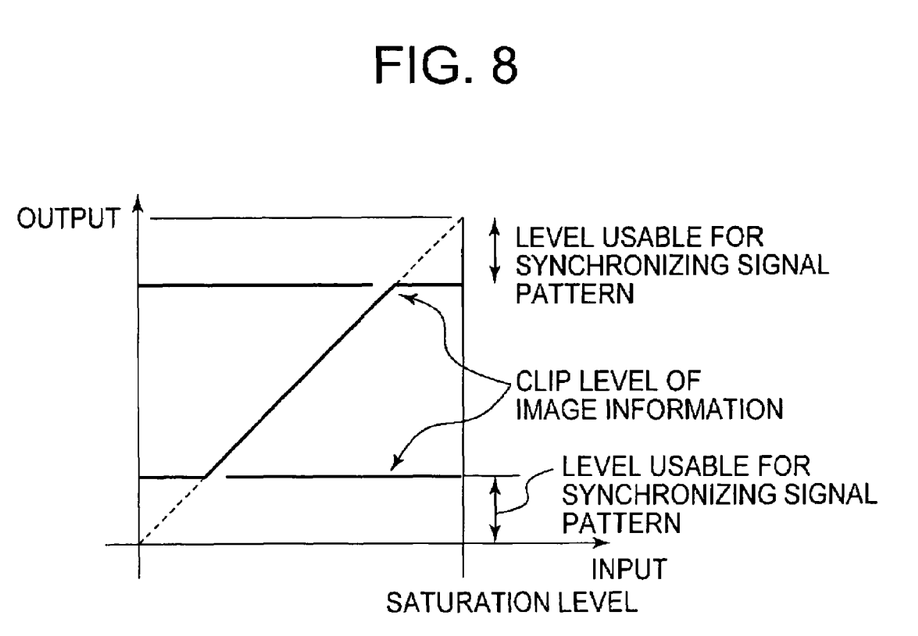
FIG. 8 is a diagram showing a signal level of image information for explaining another example of the clipping operation of the image information in the clipping circuit shown in FIG. 4.

Therefore, as shown in FIG. 8 illustrating the signal levels of the image information, image information of a low-intensity portion may be clipped by the clipping circuit 25c simultaneously with the image information of the high-intensity portion. For example, it is also possible to allocate a clipped signal pattern in the high-intensity range as a horizontal synchronizing signal and to allocate a clipped signal pattern in the low-intensity range as a vertical synchronizing signal. In this condition, the horizontal synchronizing signal and the vertical synchronizing signal exist in the same high-frequency band as for the image information and there is a large difference in the signal level between the synchronizing signals, thereby enabling the receiver to easily distinguish between the horizontal and vertical synchronizing signals. Moreover, there can be a case where transmit data is modulated so as to be of higher frequency. If so, it can be modulated either after or before the synchronizing signals are added.

Figure 9:
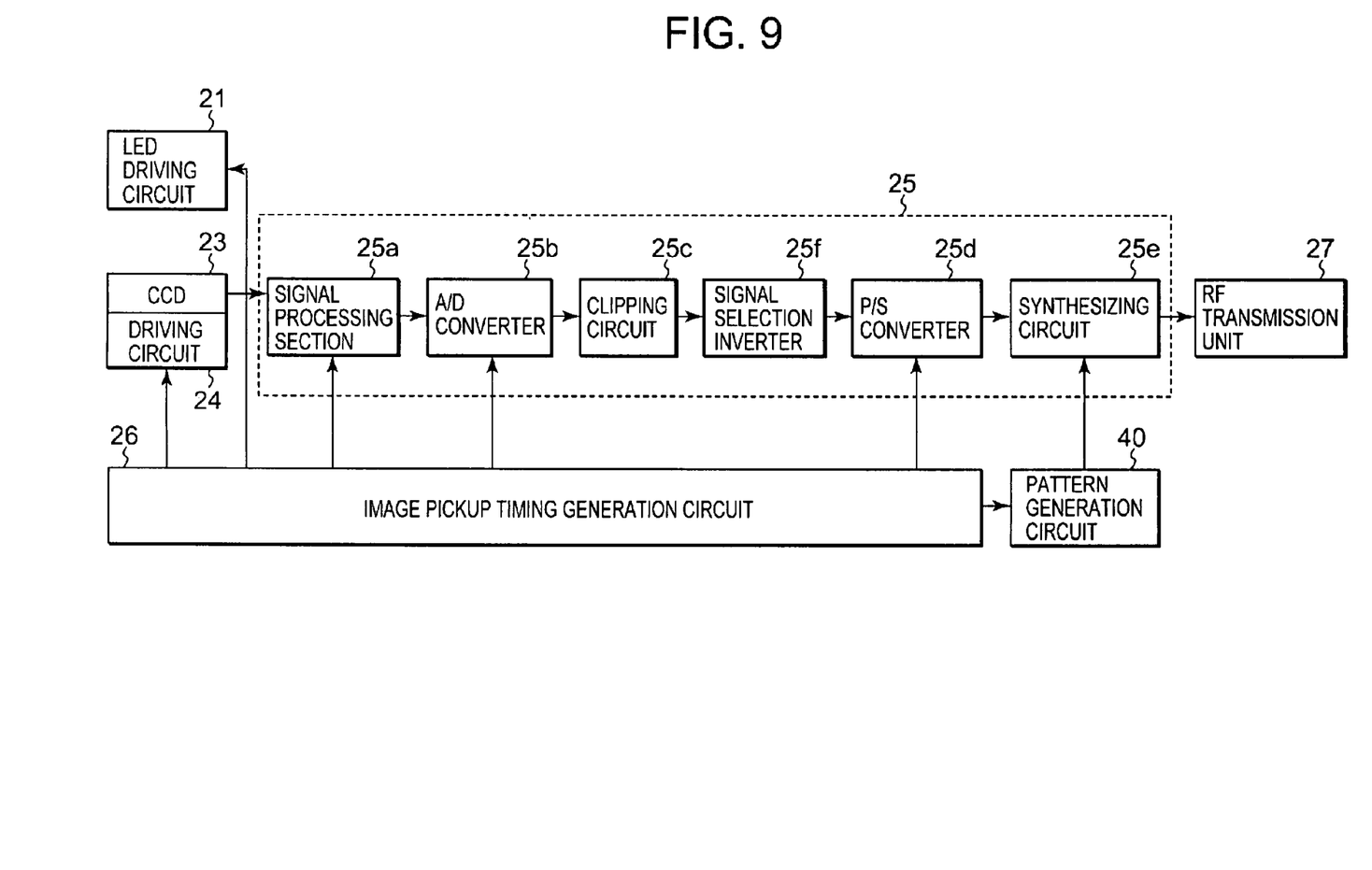
FIG. 9 is a block diagram showing a second embodiment of the image pickup timing system shown in FIG. 3.
Figure 10:
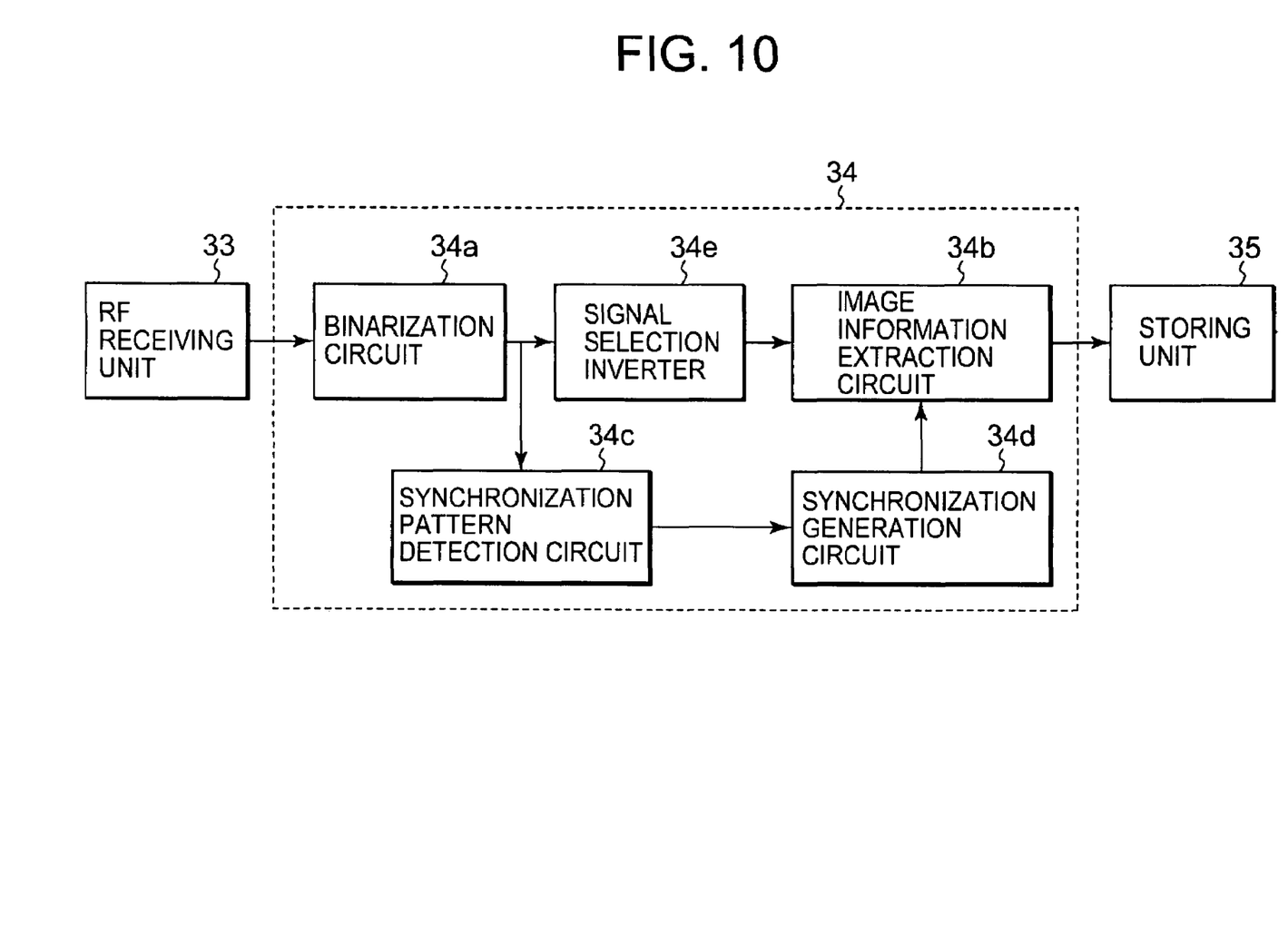
FIG. 10 is a block diagram showing a second embodiment of a detailed configuration of the image processing unit in the external device shown in FIG. 2.

Referring to FIG. 9, there is shown a block diagram of the image pickup timing system shown in FIG. 3 in a second embodiment. Referring to FIG. 10, there is shown a block diagram of a detailed configuration of the image processing unit in the external device shown in FIG. 2.

In the second embodiment, the image pickup timing system and the image processing unit differ from those shown in FIG. 4 and FIG. 6 as described below. The image pickup timing system differs from one shown in FIG. 4 in that it is provided with a signal selection inverter 25f in the subsequent stage of a clipping circuit 25c of a signal processing circuit 25. The signal selection inverter 25f selects image information on signal patterns of relatively high frequencies out of the acquired image information and converts the specific signal patterns to signal patterns of a high-intensity portion clipped by the clipping circuit 25c. The signal selection inverter 25f selects the image information on the specific signal patterns only and converts the specific signal patterns to the signal patterns of the high-intensity portion by bit-inverting. It passes image information on other signal patterns without selection thereof. The clipping circuit 25c, the signal selection inverter 25f, and a pattern generation circuit 40 constitute a first allocating section according to the present invention, and the signal selection inverter 25f has a function of a first converting section.

In this embodiment, the image processing unit differs from the image processing unit 34 in the first embodiment in that it is provided with a signal selection inverter 34e as a second allocating section for converting the image information, which has been converted to the signal patterns of the high-intensity portion by the signal selection inverter 25f, to the original specific signal patterns in the subsequent stage of a binarization circuit 34a of the image processing unit 34. Similarly to the signal selection inverter 25f, the signal selection inverter 34e also selects image information on the signal patterns of the high-intensity portion only and converts the signal patterns of the high-intensity portion to the specific signal patterns by bit-inverting. It passes image information on other signal patterns without selection thereof.

More specifically, in the second embodiment, the signal selection inverter 25f of the signal processing circuit 25 converts the image information on the signal patterns of relatively high frequencies out of the image information acquired by an imaging section 22 of a capsule type endoscope 2 to the image information on the signal patterns of the high-intensity portion and wirelessly transmits it from an RF transmission unit 27. After detecting the signal patterns of the high frequencies, a receiver 3 converts the image information on the signal patterns of the high-intensity portion to the original specific signal patterns by using the signal selection inverter 34e of the image processing unit 34 to exchange the signal patterns of synchronizing signals and the signal patterns of image information. Thus, it becomes possible to generate the synchronizing signals made of the signal patterns of higher frequencies and to set the synchronizing signals to signal patterns in the same high-frequency band as for image signals and not used for the image signals, thereby preventing a fluctuation in the DC level of signals and permitting a wider margin for a threshold for binarization. Therefore, the receiver 3 achieves more stable binarization of synchronizing signals and thus acquires favorable image signals.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An imaging device comprising:
a lighting section for emitting an illumination light for illuminating an inside of a test body;
an imaging section for acquiring image information on an inside of the test body illuminated by the lighting section;
a clipping section for clipping the image information in a predetermined intensity range;
a first allocating section for allocating a signal level of the image information in the predetermined intensity range acquired by the imaging section to a synchronizing signal comprising a horizontal synchronizing signal and a vertical synchronizing signal, both of which and the image information are set in the same frequency band; and
a radio transmission section for wirelessly transmitting the synchronizing signal allocated by the first allocating section and the image information.

2. The imaging device according to claim 1, wherein the first allocating section includes:
a first converting section for converting the signal level of a specific part of the image information to the signal level clipped by the clipping section; and
a setting section for setting the signal level of the specific part of the image information as the synchronizing signal.

3. The imaging device according to claim 1, wherein:
the radio transmission section transmits wirelessly the image information with the horizontal synchronizing signal and the vertical synchronizing signal, and
the first allocating section comprises: a pattern generation section for allocating the image information clipped by the clipping section as a horizontal synchronizing signal and a vertical synchronizing signal, both of which are set in the same frequency band as the image information.

4. The imaging device according to claim 3, wherein the clipping section clips the image information represented by signal patterns.

5. The imaging device according to claim 3, wherein the predetermined intensity range is an end portion of intensities of the image information.

6. The imaging device according to claim 3, wherein the predetermined intensity range is a high-intensity portion of intensities of the image information.

7. The imaging device according to claim 3, wherein the predetermined intensity range is a low-intensity portion of intensities of the image information.

8. The imaging device according to claim 3, wherein the first allocating section further comprises a signal selection inverter in the subsequent stage of the clipping section for selecting the image information on signal patterns of relatively high frequencies out of the acquired image information, and converting the specific signal patterns to signal patterns of a high-intensity portion clipped by the clipping section.

9. A medical device comprising an imaging device to acquire information on an inside of a test body and a receiver capable of receiving a radio signal transmitted from the imaging device outside the test body, wherein:
the imaging device comprises:
a lighting section for emitting an illumination light for illuminating the inside of the test body;
an imaging section for acquiring image information on the inside of the test body illuminated by the light section;
a clipping section for clipping the image information in a predetermined intensity range;
a first allocating section for allocating a signal level of the image information in the predetermined intensity range acquired by the imaging section to a synchronizing signal comprising a horizontal synchronizing signal and a vertical synchronizing signal, both of which are set in the same frequency band as the image information; and
a radio transmission section for wirelessly transmitting the synchronizing signal allocated by the first allocation section and the image information; and
the receiver includes:
a receiving section for receiving the radio signal wirelessly transmitted from the radio transmission section;
an extracting section for extracting the synchronizing signal from the received radio signal; and
a second allocating section for allocating the another signal level allocated by the first allocating section to the signal level of the image information.

* * * * *